United States Patent [19]

Elliott et al.

[11] Patent Number: 4,570,630
[45] Date of Patent: Feb. 18, 1986

[54] MEDICAMENT INHALATION DEVICE

[75] Inventors: Roderick D. Elliott, Burnham; Phillip J. Gardiner, High Wycombe, both of England

[73] Assignee: Miles Laboratories, Inc., Elkhart, Ind.

[21] Appl. No.: 621,787

[22] Filed: Jun. 18, 1984

Related U.S. Application Data

[63] Continuation-in-part of Ser. No. 519,912, Aug. 3, 1983, abandoned, which is a continuation of Ser. No. 317,837, Nov. 3, 1981, abandoned.

[51] Int. Cl.[4] .................................. A61M 15/00
[52] U.S. Cl. ................................... 128/203.15
[58] Field of Search ............ 128/203.15, 200.14; 604/57, 58; 222/363, 362, 370, 193, 194

[56] References Cited

U.S. PATENT DOCUMENTS

| 2,470,298 | 5/1949 | Fields | 128/203.15 |
| 2,587,215 | 2/1952 | Priestly | 128/203.15 |
| 3,949,751 | 9/1976 | Birch et al. | 128/203.15 |
| 4,184,258 | 1/1980 | Barrington et al. | 128/203.15 |
| 4,200,099 | 4/1980 | Guenzel et al. | 128/203.15 |
| 4,240,418 | 12/1980 | Rosskamp et al. | 128/203.15 |
| 4,274,403 | 6/1981 | Struve | 128/203.15 |

FOREIGN PATENT DOCUMENTS

| 0079478 | 10/1982 | European Pat. Off. | 128/203.15 |
| 2041763 | 9/1980 | United Kingdom | 128/203.15 |
| 628931 | 10/1978 | U.S.S.R. | 128/203.15 |

Primary Examiner—Henry J. Recla
Assistant Examiner—Karin M. Reichle
Attorney, Agent, or Firm—Louis E. Davidson

[57] ABSTRACT

An inhalation device for dispensing medicament has a horizontally rotatable medicament delivery member positioned between a medicament storage chamber and an air inhalation chamber where the medicament is suspended in air for subsequent inhalation by a patient.

4 Claims, 8 Drawing Figures

MEDICAMENT INHALATION DEVICE

BACKGROUND AND PRIOR ART

This is a continuation-in-part application of U.S. Pat. application Ser. No. 519,912, filed Aug. 3, 1983, now abandoned, which was a continuation application of U.S. Pat. application Ser. No. 317,837, filed Nov. 3, 1981, now abandoned.

Hypersensitive individuals undergo an altered state as a result of contact with the antigens from an allergen, leading to the formation of antibodies to the allergen. Subsequent contact with one of those antigens or a structurally similar substance can evoke in an allergic individual a pathological reaction, due to the presence of such antibodies. A prominent manifestation includes bronchial asthma, characterized by obstruction of the lung airway passages.

In order to reduce these undesirable allergic responses, various medicaments which have an antiallergic characteristic have been administered to patients.

It has been firmly established that the optimal route of medicament administration to provide therapeutic relief against such allergic respose is by inhalation, which provides local administration to the lung airway lumen. Inhalation provides convenience and speed of action and often requires only a small dose of the pharmacologically active agent.

One type of inhalation device involves the use of conventional pressurized aerosol canisters. Some patents, however, find it difficult to synchronize inhalation through the mouth with activation of the canister. Substances used as propellants in such aerosols may include fluorocarbons, which are safe when inhaled in small quantities, but may predispose individuals to ventricular arrythmias if inhaler usage is excessive.

Various inhalation devices have been proposed and used which are capable of delivering dry powder medicaments into the patients'lungs. Typical of such inhalation devices are those described in U.S. Pat. Nos. 3,507,277; 3,635,219; 3,669,113 and 3,870,046.

Many inhalation devices rely upon the motion of inhaled air to cause dispersion of the medicament into the air being inhaled. For example, U.S. Pat. No. 4,200,099 to Guenzel et al., describes such a device wherein a venturi effect is utilized to effect efficient dispersion and inhalation. Similarly, U.S. Pat. No. 4,240,418 discloses use of venturi-shaped chambers. However, many of such prior art devices are susceptible to clogging, are complicated and are difficult to operate. Drug delivery by inhalation requires a device which is relatively simple in construction, inexpensive and easy to use by young and older individuals, is compact in size, and also capable of delivering a metered dose of various sized particles. There is a need in the allergy field for such a simplified and efficient inhalation device.

SUMMARY OF THE INVENTION

The present invention is an inhalation device comprising, in combination, a medicament chamber capable of storing finely-divided medicament therein, an air inhalation chamber, and a substantially cylindrical medicament delivery member communicating between said medicament chamber and said air inhalation chamber, said medicament chamber having a downwardly directed funnel-shaped bottom wall having a bottom opening therein and having an upwardly extending sidewall from said bottom wall with a closed top to define said chamber, said air inhalation chamber having a longitudinally extending outer wall having a top opening therein and two opposiing ends, a side air inlet means formed in a closed end wall at the first of said ends and a mouthpiece air outlet means having a transverse screen associated therewith located at the second of said ends opposite to said air inlet means, said side air inlet means comprising a passage extending through said end wall at an oblique angle with respect to the plane of orientation of said first opposed end, the longitudinal axis of said passage being positioned so as to intersect the outer wall of said air inhalation chamber at a point directly beneath and opposite to said top opening therein, said medicament delivery member having a cavity of predetermined volume therein with an opening therefor and being horizontally rotatable between a first position wherein said cavity opening is vertically aligned with said bottom opening of said medicament chamber so as to fill said cavity with a predetermined dose of medicament from said medicament chamber and a second position wherein said cavity opening is vertically aligned with said top opening of said air inhalation chamber so as to enable the predetermined dose of medicament to pass into said inhalation chamber, whereby inhalation of air from said air inlet means into said air inhalation chamber and from said mouthpiece air outlet means effects movement of said predetermined dose of medicament through said air inhalation chamber and from said mouthpiece.

DESCRIPTION OF THE INVENTION

Figure 1:
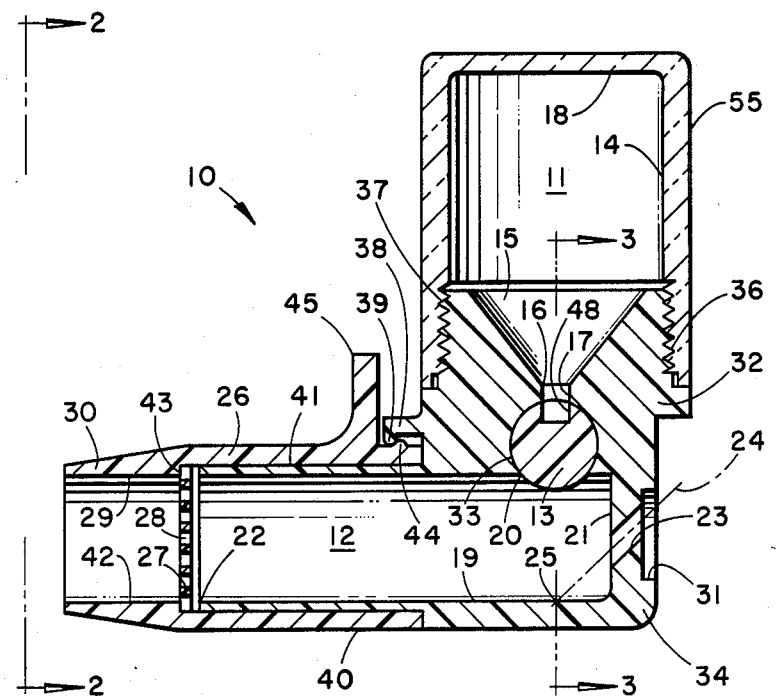
FIG. 1 is a vertical cross-sectional view of the medicament inhalation device of the present invention.
Figure 3:
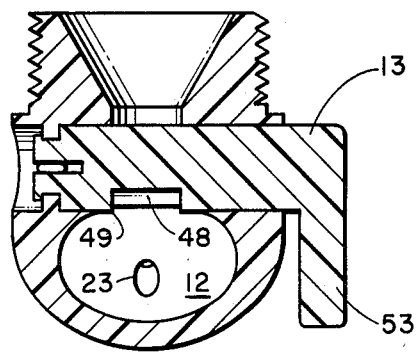
FIG. 3 is a vertical cross-sectional view of a portion of the apparatus of FIG. 1 taken along Line 3—3 with the medicament delivery member rotated 180 degrees from the position of FIG. 1.
Figure 4:
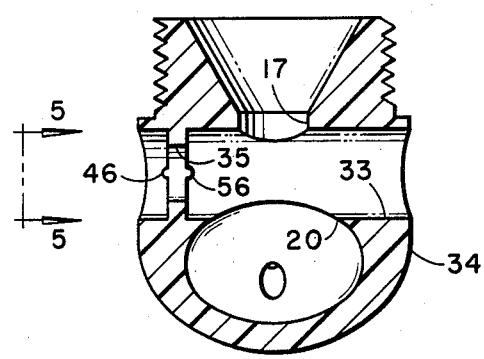
FIG. 4 is a vertical cross-sectional view similar to FIG. 3 with the medicament delivery member removed.

As shown in FIG. 1, illustrated embodiment of the present invention comprises a medicament inhalation device 10 having a medicament chamber 11, an air inhalation chamber 12, and a substantially cylindrical, metered dose medicament delivery member 13. Medicament chamber 11 is generally vertically cylindrical in shape and is formed with sidewall 14 and a downwardly directed funnel-shaped bottom wall portion 15 having a bottom opening 16 therein communicating with a vertical passage 17. Chamber 11 is closed at the top portion 18. Air inhalation chamber 12 has a horizontally longitudinally extending outer wall 19 with a top opening 20 therein communicating with vertical passage 17. Air inhalation chamber 12 has a first closed end wall 21 and a second open end 22 located opposite to said first end wall 21. First end wall 21 has a side air inlet means formed by a passage 23 extending through the end wall 21 at an oblique angle with respect to the plane of orientation of end wall 21. The longitudinal axis 24 of passage 23 is positioned so as to intersect the outer wall 19 at a point 25 directly beneath and opposite to the top opening 20 of chamber 12. The outer end of passage 23 can communicate with a recess 31 located in first end wall 21. As shown in FIGS. 3 and 4, chamber 12 has an elliptical cross-section shape.

Figure 5:
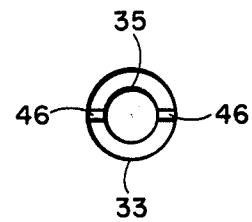
FIG. 5 is an end view of a portion of the apparatus taken along Line 5—5 of FIG. 4.

Chamber 12 is conveniently formed in a generally L-shaped single member 34 having the horizontally positioned wall 19 and a vertical portion 32 having the funnel-shaped portion 15 and vertical passage 17 formed therein. Transverse horizontal passage 33 having a circular cross-section is formed in member 34 normal to vertical passage 17 and the longitudinal axis of chamber 12. As shown in FIG. 4, passage 33 has a constriction 35 located therein near one end thereof. As shown in FIG. 5, constriction 35 has two radial ribs or elongated ridges 46 located on the outer surface thereof diametrically from each other. These ribs extend radially from the opening in constriction 35 toward the wall of passage 33. As shown in FIG. 4, constriction 35 also has two similar radial ribs or elongated ridges 56 located on the opposite side of constriction 35 from ribs 46. Vertical portion 32 of member 34 has external threads 36. The medicament chamber 11 is conveniently formed by placing cylindrical member 55 having a closed end 18 and internal threads 37 in mating relationship with the threads 36 of vertical portion 32 of member 34. It is understood that member 55 can alternatively be attached to member 34 by other means, such as interlocking snap-on devices. Vertical portion 32 has a horizontal extension 38 with a lower detent 39 depending therefrom.

Figure 2:
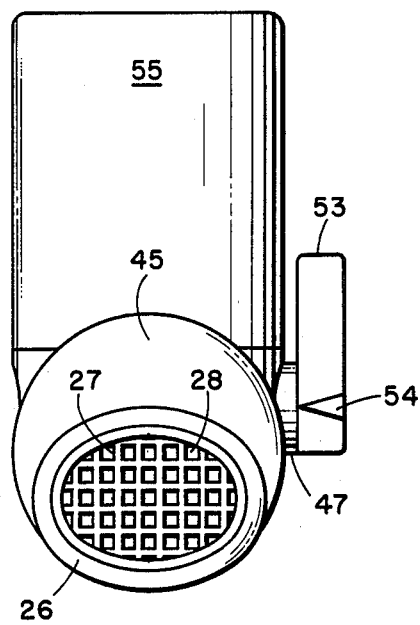
FIG. 2 is a front elevational view of the apparatus of FIG. 1 taken along Line 2—2.

A mouthpiece air-outlet member 26 is placed over the open end 22 chamber 12 of member 34. Member 26 has a horizontally longitudinally extending wall 40 surrounding an internal stepped outlet passage 49. This stepped passage has a first portion 41 having internal dimensions slightly larger than those of the outer wall 19 of chamber 12 so that it can conveniently slip over wall 19. The stepped passage has a second portion 42 having internal dimension substantially the same as those of chamber 12 and open end 22. Step 43 is located at the junction between first portion 41 and second portion 42. Transverse screen 27 having a plurality of openings 28 therein is located in first portion 41 at step 43. Screen 27 is intended to break up clumps of medicament particles. Each of said openings 28 has a cross-sectional dimension slightly larger than the corresponding dimension of the largest clump of medicament particles intended to pass through chamber 12. The outlet portion 30 of mouthpiece member 26 is externally tapered so as to conveniently fit into a human mouth. As shown in FIG. 2, mouthpiece member 26 and screen 27 have a generally elliptical cross-sectional shape which corresponds to the shape of chamber 12. Member 26 has an external detent 44 projecting upward from wall 40 near the end of member 26 opposite from outlet portion 30. Member 26 preferably has a projection 45 of generally circular shape extending upward from wall 40. This projection prevents member 26 from being swallowed by a patient if it is detached from the device 10 for any reason. In the assembly of device 10, member 26 is slipped over wall 19 and pushed until detent 44 passes under and is engaged by detent 39. Screen 27 then covers open end 22 of chamber 12.

Figure 6:
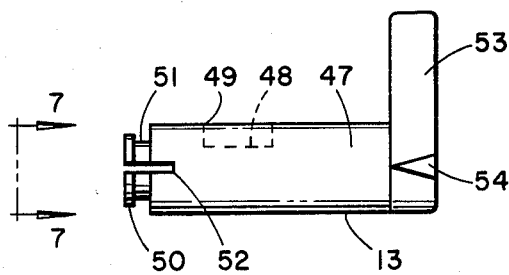
FIG. 6 is a side elevational view of the medicament delivery member.
Figure 7:
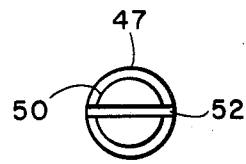
FIG. 7 is an end view of the medicament delivery member taken along Line 7—7 of FIG. 6.
Figure 8:
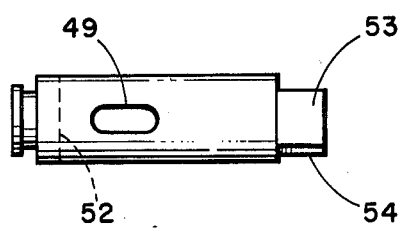
FIG. 8 is a side elevational view of the medicament delivery member rotated 90 degrees from the position of FIG. 6.

Metered dose medicament delivery member 13 is shown in FIGS. 6, 7 and 8. Member 13 has a main cylindrical portion 47 with an elongated slot cavity or recess 48 having an opening 49 thereof formed in the longitudinally extending exterior surface of said member 13. As shown in FIG. 6, the vertical axis of cavity 48 is normal to the exterior surface of member 13. Cavity 48 has a predetermined volume. As shown in FIG. 8, the elongated cavity 48 and opening 49 are parallel to the longitudinal axis of portion 47. Member 13 has an axial extension 50 with a reduced cross-sectional portion 51 located at one end thereof. A transverse slot 52 is formed in member 13 and extends longitudinally through extension 50 and into cylindrical portion 47. At the other end of member 13 opposite to extension 50 there is an arm 53 projecting radially from member 13. On one side of arm 53 is an indicator market, such as arrow 54. In the assembly of device 10, member 13 is placed into passage 33 of member 34 and pushed inward until extension 50 passes through constriction 35 and constriction 35 mates against reduced portion 51. This is shown in FIG. 3. In this position the central vertical axis of cavity 48 coincides with the central vertical axis of opening 16 and the central vertical axis of opening 20. When arm 53 is in the position shown in FIG. 3, the opening 49 of cavity 48 is vertically aligned with opening 20 of chamber 12. In this position slot 52 is aligned with ribs 46 and 56 which allows the ribs 46 and 56 both to be able to simultaneously lie in slot 52 and assist in maintaining the delivery member 13 in this arrangement, and arrow 54 is aligned with an indicator (not shown) on the outer surface of member 34. When arm 53 is horizontally rotated to a position 180 degrees from that shown in FIG. 3, the opening 49 of cavity 48 will be in the position shown in FIG. 1 vertically aligned with the bottom opening 16 of medicament chamber 11. In this position the ribs 46 and 56 will again both be able to lie in slot 52, and the arrow 54 on arm 53 will be aligned with another indicator (not shown) on the outer surface of member 34. The cross-sectional dimensions of opening 16 and passage 17 are preferably the same as those of opening 49 of cavity 48.

The member 34, mouthpiece 26, member 55 and screen 27 are preferably formed from suitable rigid organoplastic materials, such as polystyrene, polyethylene, polypropylene, styrene-acrylonitrile copolymers, polycarbonate, acetal copolymers, nitrile-acrylonitrile-styrene copolymers, polymethylpentene, polyacrylate, polymethacrylate and the like. Member 34, mouthpiece 26 and screen 27 are preferably formed from high impact polystyrene. Member 55 is preferably optically transparent. Member 13 is preferably formed from a softer organoplastic, such as the polyamides known as nylon.

In the manufacture of the device of this invention, member 55 is filled with the desired finely-divided medicament. Member 34 is inverted from the position shown in FIG. 1 while member 55 containing the medicament in chamber 11 is screwed onto the threads 36 of member 34. The device is then held in the position shown in FIG. 1. Arm 53 is rotated to an upwardly extending position which places cavity 48 in the first position shown in FIG. 1 so as to fill cavity 48 with a predetermined dose of medicament from chamber 11. It is preferable to tap the device to enable complete flow of medicament into cavity 48. Arm 53 is then horizontally rotated 180 degrees to the second position shown in FIG. 3. Cavity 48 is now vertically aligned with the top opening 20 of chamber 12 so as to enable the predetermined dose of medicament to drop into inhalation chamber 12 where it is deposited on the outer wall 19 directly beneath opening 20. It is also preferably to tap the device to enable complete removal of medicament from cavity 48. A patient then places his mouth over the mouthpiece 26 and inhales. The resulting inhalation of air from air inlet means 23 causes the air stream to strike the medicament on the bottom of chamber 12 causing such medicament to become suspended in the air stream. The suspended dose of medicament then moves through the screen 27 and out of the mouthpiece into the respiratory tract of the patient.

The finely-divided medicaments used in the device of the present invention can range from about 0.5 to 5 microns in particle size as a preferred range for efficient administration to the lung airway lumen. The size of the cavity 48 in delivery member 13 will be dependent upon the desired dose of the particular medicament. It is intended that chamber 11 hold about 2–10 g. of medicament so that the device can be used to deliver about 200 doses. Different color coded delivery members 13 could be employed to designate different dose cavity sizes. Also different sizes of member 55 can be used for various storage capacities.

When the device of the present invention is not being used by a patient, removable cover means (not shown) can fit into recess 31 and the inlet of mouthpiece 26 to seal and protect them.

What is claimed is:

1. An inhalation device comprising a medicament housing defining a medicament chamber therein capable of storing finely-divided medicament, said medicament housing having first and second opposite end walls and side wall means extending therebetween, said first end wall defining a bottom wall and having a central opening therein, said side wall means defining a passage extending from the opening in said first end wall to said second end wall, said passage comprising a first portion adjacent said second end wall and having a constant cross-section along the length thereof greater than the cross-section of said opening and a second portion extending from the first portion of said passage to said opening and tapering in cross-section from the cross-section of said first portion to the cross-section of said opening, said passage defining said medicament chamber, said medicament housing having means for permitting placement of medicament in said chamber;

an air inhalation housing defining an air inhalation chamber therein, said air inhalation housing including a tubular side wall means having a constant cross-section along the length therof, opposite first and second ends and a radial opening therein adjacent the first end thereof, said air inhalation housing further including an end wall with air inlet means formed therein at the first end of said tubular side wall means and being open at the second end of said tubular side wall means, said tubular side wall means, said end wall and said second open end defining said air inhalation chamber, an elongate mouthpiece having a screen mounted transversely therein connected to said second end, said air inlet means comprising a passage extending through said end wall at an oblique angle with respect to the plane of orientation of said end wall and being positioned such that the longitudinal axis of said passage intersects the wall of said tubular side wall means at a point directly opposite to and across from the opening therein; and a substantially cylindrical medicament delivery member defining a recess of predetermined volume formed in the longitudinally extending exterior surface of said delivery member, said delivery member being rotatably mounted between the bottom wall of said medicament housing and the tubular said wall means of said air inhalation housing adjacent the radial opening therein such that the recess in said delivery member communicates with the opening in said medicament housing bottom wall in one position and the radial opening in said tubular side wall means in a second position whereby, when said medicament chamber is upright with the first end wall below the second end wall, said delivery member is horizontally rotatable between said first position wherein the recess therein communicates with said opening in the bottom wall of said medicament chamber so as to fill said recess with a predetermined dose of medicament from said medicament chamber and said second position wherein said recess communicates with the radial opening in the tubular side of said air inhalation housing so as to enable the predetermined dose of medicament to pass into said inhalation chamber, and inhalation of air from said air inlet means into said air inhalation chamber and out of said mouthpiece effects movement of said predetermined dose of medicament through said air inhalation chamber and out of said mouthpiece.

2. An inhalation device according to claim 1 wherein the recess of the medicament delivery member comprises an elongate slot.

3. An inhalation device according to claim 1 wherein the air inhalation chamber and the mouthpiece both have an elliptical cross-section.

4. An inhalation means according to claim 1 having external means for indicating the position of the recess with respect to the medicament chamber and the air inhalation chamber.

* * * * *